United States Patent [19]

Madsen et al.

[11] Patent Number: 5,029,729

[45] Date of Patent: * Jul. 9, 1991

[54] METHOD OF DISPENSING VAPOR TO THE AIR IN A ROOM AND AN APPARATUS FOR CARRYING OUT THE METHOD

[75] Inventors: Jens Madsen, Abyhoj; Svend S. Kaae, Aarhus, both of Denmark

[73] Assignee: Milliken Denmark A/S, Morke, Denmark

[*] Notice: The portion of the term of this patent subsequent to Apr. 21, 2004 has been disclaimed.

[21] Appl. No.: 333,667

[22] Filed: Apr. 4, 1989

Related U.S. Application Data

[60] Continuation of Ser. No. 920,749, Oct. 20, 1986, which is a division of Ser. No. 754,840, Jul. 15, 1985, Pat. No. 4,658,985.

[51] Int. Cl.⁵ .................. B67B 7/00; G04C 5/08
[52] U.S. Cl. ...................... 222/1; 222/643; 422/124
[58] Field of Search .............. 222/1, 638–639, 222/643–649; 239/66, 69–70; 261/DIG. 17; 422/124–125

[56] References Cited

U.S. PATENT DOCUMENTS

| | | | |
|---|---|---|---|
| 2,686,944 | 8/1954 | Gubelin | 422/124 |
| 2,830,142 | 4/1958 | Smith | 200/38 A |
| 2,855,476 | 10/1958 | Garrard | 200/38 A |
| 3,055,552 | 9/1962 | Emmons | 222/639 |
| 3,290,112 | 12/1966 | Gillenwater et al. | 43/129 |
| 3,298,674 | 1/1967 | Gilbertson | 261/30 |
| 3,351,240 | 11/1967 | Gray | 222/646 |
| 3,524,471 | 8/1970 | Bresser | 137/624.12 |
| 3,633,881 | 1/1972 | Yurdin | 261/24 |
| 3,796,541 | 3/1974 | Gentil | 422/108 |
| 3,949,241 | 4/1976 | Maute | 307/141 |
| 3,974,941 | 8/1976 | Mettler | 222/646 |
| 3,990,848 | 11/1976 | Corris | 422/49 |
| 3,993,444 | 11/1976 | Brown | 422/116 |
| 4,059,422 | 11/1977 | Steiner | 55/418 |
| 4,078,891 | 3/1978 | Madjar | 422/116 |
| 4,166,087 | 8/1979 | Cline et al. | 261/96 |
| 4,184,612 | 1/1980 | Freyre | 222/639 |
| 4,213,562 | 7/1980 | Garrett et al. | 236/46 R |
| 4,658,985 | 4/1987 | Madsen et al. | 222/1 |

FOREIGN PATENT DOCUMENTS

| | | |
|---|---|---|
| 447107 | 3/1948 | Canada . |
| 0038598 | 10/1981 | European Pat. Off. . |
| DE2840690 | 11/1982 | Fed. Rep. of Germany . |
| 1231262 | 5/1971 | United Kingdom . |
| 1449448 | 9/1976 | United Kingdom . |
| 1598372 | 9/1981 | United Kingdom . |
| 2080111 | 2/1982 | United Kingdom . |
| 2119499 | 11/1983 | United Kingdom . |
| 8100680 | 11/1981 | World Int. Prop. O. . |

Primary Examiner—Michael S. Huppert

[57] ABSTRACT

By method of dispensing vapor, preferably perfumed vapor, to the air in a room from a vapor dispensing substance, vapor is dispensed by means of an electrically controlled control device for controlling the vapor dispensation of the vapor dispensing substance, and an electrical circuit for controlling the current supply to the control device. By the fact that the electrical circuit is supplying a time controlled, gradually increasing current supply to the control device in time periods with intermediate periods of no current supply to the control device is achieved that the concentration of the vapor dispensed is kept at a constant level, until the vapor dispensation substance has been used up.

6 Claims, 3 Drawing Sheets

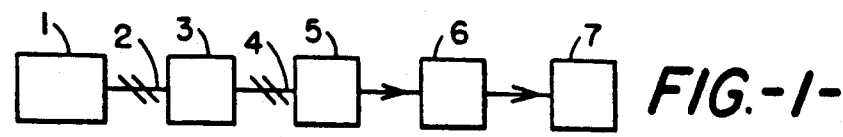
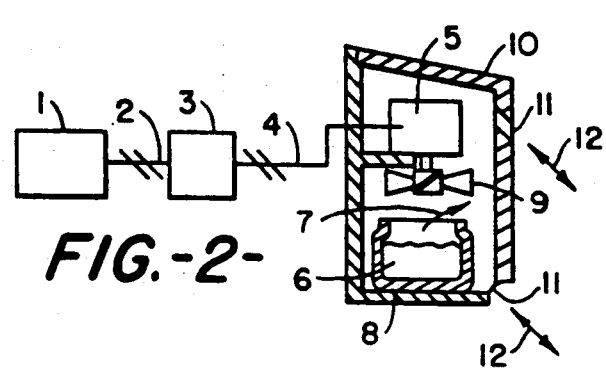
FIG.-2-
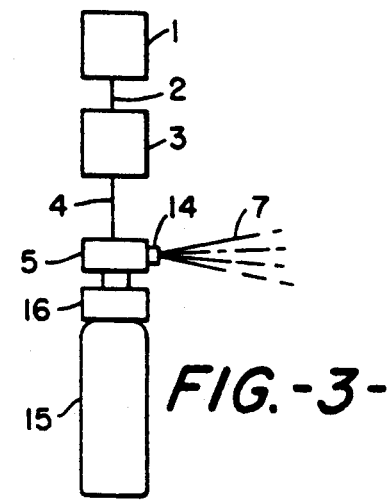
FIG.-3-
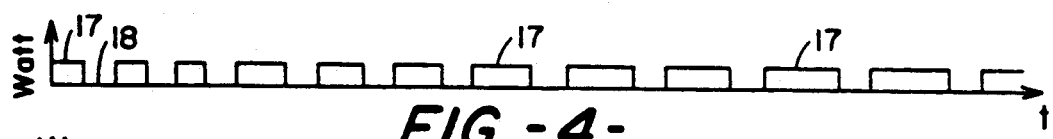
FIG.-4-
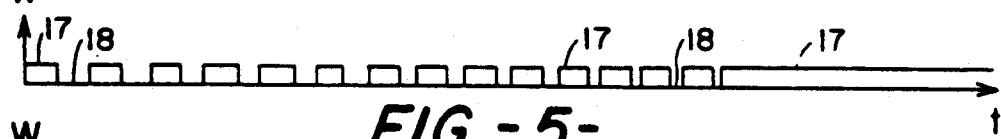
FIG.-5-
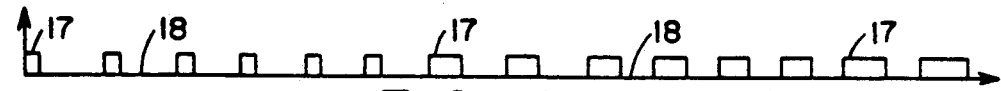
FIG.-6-
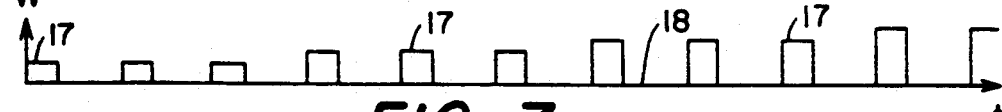
FIG.-7-
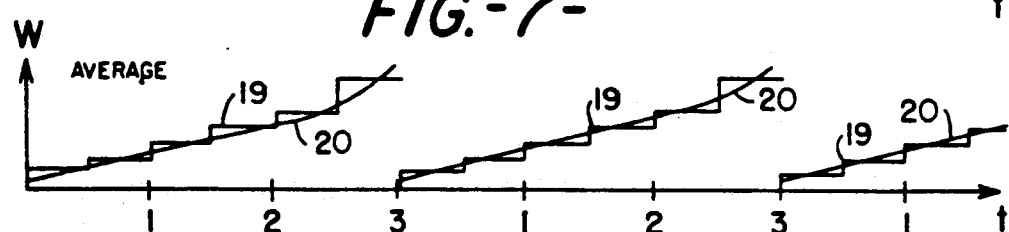
FIG.-8-
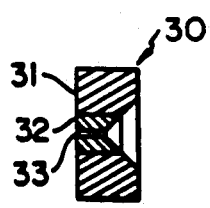
FIG.-9-
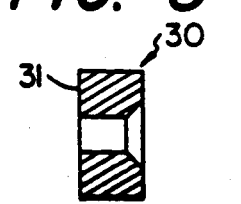
FIG.-10-
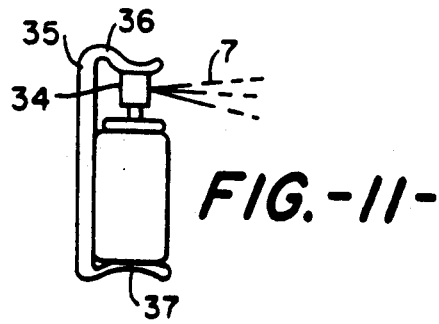
FIG.-11-

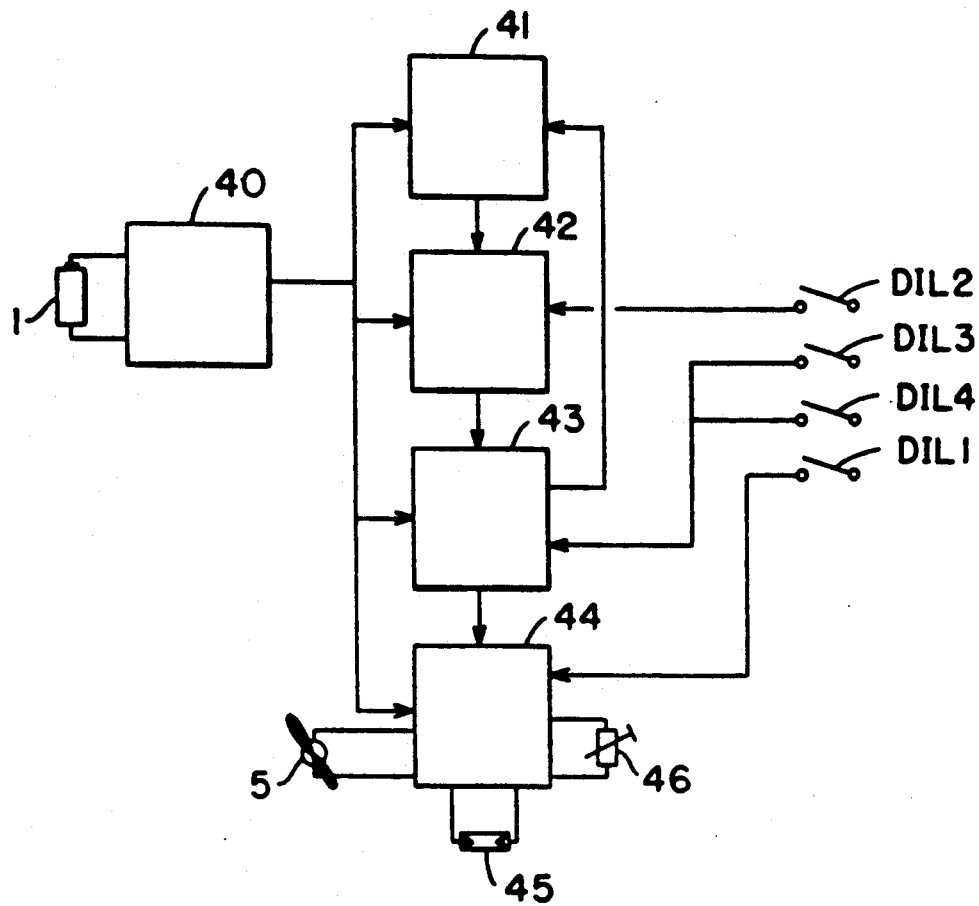
FIG.-12A-

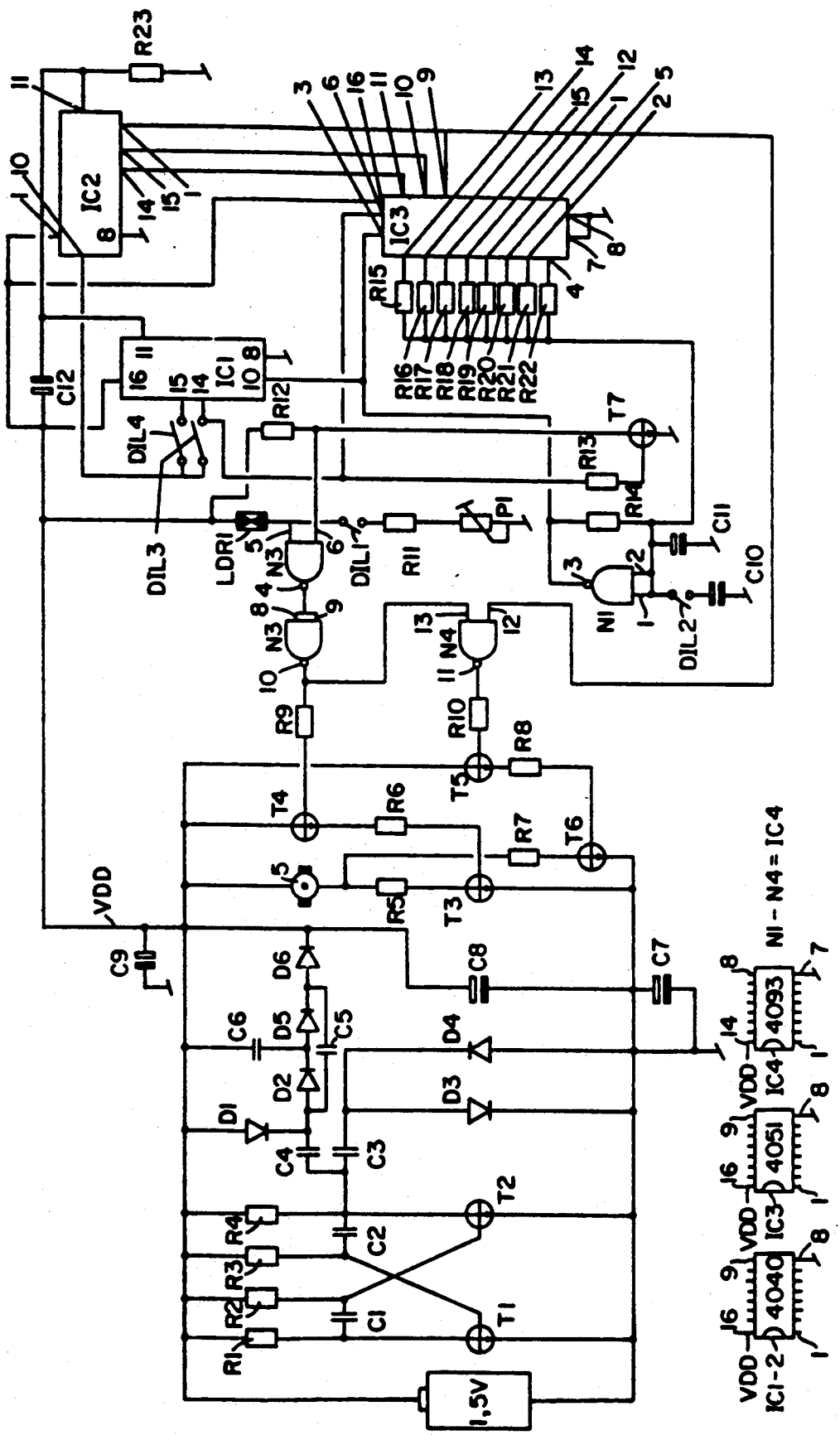
FIG.-12B-

METHOD OF DISPENSING VAPOR TO THE AIR IN A ROOM AND AN APPARATUS FOR CARRYING OUT THE METHOD

This is a continuation of application Ser. No. 06/920,749 filed Oct. 20, 1986 for METHOD OF DISPENSING VAPOUR TO THE AIR IN A ROOM AND AN APPARATUS FOR CARRYING OUT THE METHOD, which is a division of application Ser. No. 754,840, filed July 15, 1985, now U.S. Pat. No. 4,658,985.

This invention relates to method of dispensing vapor into the air in a room.

The method is achieved such that the vapour dispensed by the method gets a substantially constant concentration level in the room wherein the method is carried out, until the vapour dispensing substance is substantially used up, in spite of the fact that the vapour dispensability of the substance decreases to a minimum level at the using up time from a maximum level when starting the use of the substance.

The invention also deals with an apparatus for carrying out the method of dispensing vapour to the surroundings of the apparatus.

The invention will now be described in more detail in connection with some examples and with reference to the drawing wherein FIG. 1 shows a principle diagram for the method and apparatus for carrying out said method, FIG. 2 an embodiment of an apparatus according to the invention, FIG. 3 a second embodiment of the apparatus according to the invention, FIG. 4-7 examples of effect-time-diagrams for the control device, FIG. 8 a diagram showing the average effect supplied to the control device from the electric circuit, in the using up time of two successive substances, FIG. 9 an embodiment of a spray can nozzle at the start of the vapour dispensation, FIG. 10 the nozzle of FIG. 9 at the end of the vapour dispensation, FIG. 11 a device for vapour dispensation during use of the nozzle of FIGS. 9 and 10, FIG. 12A a block diagram for the electric circuit with current supply source, and FIG. 12B electric diagram according to the one of FIG. 12A.

In FIG. 1 a current supply supplies current via an electric connection 2 to an electronic circuit 3 which is adapted to supply a time controlled, gradually increasing current supply via an electric connection 4 to a control device 5 for time periods with intermediate periods without current supply via the electric connection 4 to the control device 5 from the electronic circuit 3. The control device 5 thus electrically controlled serves for controlling the vapour dispensation, preferably perfumed vapour, from a vapour dispensing substance 6 to the air in a room, which should be supplied with vapour dispensation 7. Caused by the special control of the control device by the electronic circuit, a substantially constant vapour concentration is achieved in the room in which the method is practiced, until the vapour dispensing substance 6 is substantially used up, which is due to the gradually increasing current supply to the control device 5.

FIG. 2 shows an apparatus for carrying out the method, and the apparatus comprises a vapour dispensing device which in this case comprises an upwardly open container 8 containing a predetermined volume of a vapour dispensing substance 6. In the apparatus the electrically controlled control device 5 is formed by a motor driven ventilator with a propeller 9 for getting the air in the apparatus to move and possibly blow said air against the surface of the vapour dispensing substance 6. Thereby the control device 5 controls the vapour dispensation from the vapour dispensing device 6, 8. Inside or by the apparatus the electronic circuit 3 with current supply 1 is provided, which via electric connections 2 and 4 is connected to the ventilator 5. The ventilator 5 and the vapour dispensing device 6, 8 is here shown to be arranged in a housing or casing 10 with openings 11, through which vapour 7 and the surrounding air may flow out and in respectively, as illustrated by the arrows 12. When the flow to the ventilator 5 is interrupted, substantially no vapour dispensation to the surroundings of the apparatus takes place, and the vapour dispensation is started when the ventilator 5 is started.

FIG. 3 shows a second embodiment of an apparatus with current supply 1, electronic circuit 3 and a control device 5A formed by an electromagnet controlling a valve for vapour dispensation 7 through an atomizer nozzle 14 from a spray can 15 containing an easily vapourizing, liquid vapour dispensing substance under pressure. An adaptor 16 is seen between the electromagnet 5A and the spray can 15, said adaptor being adapted to connect the interior of the spray can 15 with the electromagnet 5A. The electromagnet 5A is either performed to exert a pressing force onto a valve on the top of the spray can 15 or performed as a magnet valve being supplied with the contents of the spray can 15 and opens up for the outflow of said contents through the nozzle 14, when the electronic circuit 3 supplies current to the core of the magnet valve.

FIGS. 4-7 show more different examples of the control of the control device 5 or 5A on the electronic circuit 3. In the four systems of coordinates the current supply is illustrated on the ordinate axis as the measuring unit Watt, and the time passed t is shown on the abscissa. FIG. 4 shows stepwise increasing working period 17 with intermediate constant resting or pausing periods 18 by constant Watt consumption in the working periods 17. Thus, during the working periods 17 current is supplied to the control device 5, 5A respectively, and during the resting periods 18 said current has been interrupted. FIG. 5 shows a kind of control with constant working periods 17 and stepwise decreasing resting periods 18 at constant Watt consumption in the working periods 17, and, as appears, the resting periods 18 decreases to zero, so that the control device 5 of the apparatus at last is supplied with constant current. FIG. 6 shows an embodiment with stepwise increasing working periods 17 and simultaneously stepwise decreasing resting periods 18 at constant Watt consumption during the working periods 17. Also here the control device 5 will get a constant current supply. FIG. 7 shows an embodiment with constant working periods 17 and constant resting periods 18 but with a stepwise increasing Watt consumption during the working periods 17.

A common feature for all the kinds of control in FIGS. 4-7 is that the average Watt consumption per hour, per week or per month is even or stepwise increasing, which is illustrated in FIG. 8, where a stepwise increasing average Watt consumption is shown at the stair curve 19, and a continuously increasing Watt consumption for the control device 5 is shown at the curve 20. The numerals on the abscissa show the working time in months of the device, and, as will appear, the average Watt consumption decreases after about 3 months, which is due to the fact that the vapour dispensing substance is used up and replaced by a new substance volume simultaneously with the function of the electronic circuit 3 is reset to the starting condition, possibly by changing a battery for current supply.

FIG. 9 shows a nozzle 30 for insertion in the control button of a spray can. Said nozzle comprising an outer ring 31 which could be an integrated part of the control button itself, and a nozzle liner 32 of a material which either is very slowly dissolved by the liquid vapour dispensing substance in the spray can during its outflow through the nozzle, or is worn away very slowly by the passage of the substance through a needle-thin boring 33 in the nozzle liner. The boring 33 will during the outflow of the substance, increase its cross section successively simultaneously with the pressure in the spray can decreasing successively as a consequence of the pressure drop of the gaseous propellant, until the liquid, vapour dispensing substance is fully ejected from the spray can.

FIG. 10 shows the nozzle liner 30 before a nozzle liner 32 is inserted therein, or after the nozzle liner has been removed by the outflowing atomized substance. Such nozzle might replace the stationary nozzle 14 in FIG. 3 in connection with one of the kinds of control for the control device 5A shown in FIGS. 4, 5, or 6, whereby the working periods 17 may get a lower increase rate, or the duration of the intermediate resting periods may decrease slowlier Thereby the electronic circuit consumes less current to the control device, and a given current supply, such as a battery, may get a longer life time in the apparatus according to the invention. The nozzle shown in FIGS. 9 and 10 may, however, also be used as a nozzle in a control button 34 in a spray can 15 for vapour dispensation shown in FIG. 11, preferably perfumed vapour, whereby the spray can is arranged in a mounting loop, e.g. for wall mounting. The distance between the legs 36 and 37 of the loop 35 is thus selected that the spray can 15 when inserted therein as shown in FIG. 11 may have its valve actuated via the control button 34 for a permanent dispensation of vapour. Caused by the special material of which the nozzle liner 32 is made, and by the opening cross section and length of the boring 33 performed in accordance with the desired starting vapour volume and the spray can pressure present, the vapour dispensation 7 will achieve a constant, predetermined value, until the contents of the spray can 15 has been used up. As the opening cross section of the boring 33 is increased by tearing of the material of the nozzle liner 32, the decreasing pressure of the spray can will be compensated for. The vapour dispensation 7 may be interrupted by removing the spray can from the mounting loop 35, whereby the valve of the spray can is blocked. Said function may, of course, also be carried out by means of a control lever on the loop or by performing the loop in such a way that the spray can may be arranged in different positions in the loop, so that the spray can in the one position has its valve actuated and in its other position has its valve de-actuated.

FIG. 12A shows a block diagram for controlling a control device 5 in the form of a motor driven ventilator or a solenoid controlled valve 5A as shown in FIGS. 2 and 3. In the block diagram a current supply 1 in the form of a 1½ V battery supplies current to an unstable voltage doubler 40 which supplies an oscillator control circuit 41, an oscillator circuit 42, a counter circuit 43 and a control device circuit 44 for controlling the control device 5 in the form of a ventilator or an electromagnet. A light sensitive resistor 45 which is adjustable with a light sensitivity control 46, serves to interrupt the control device circuit, when the light intensity of the surroundings becomes too weak, so that the control device is interrupted in dark surroundings. The electronic circuit might advantageously be arranged on print together with four change-over switches DIL 1-4. In the block diagram DIL 1 is an on/off switch for light sensitivity. DIL 2 is a switch dividing the whole sequence in 2, and DIL 3 and 4 double the whole sequence without altering the working period/resting period ratio FIG. 12B shows an example of an electric diagram corresponding to the block diagram of FIG. 12A. Here the voltage doubler of FIG. 12A consists of resistors R1-R4, condensators C1-C8, transistors T1-T2 and of diodes D1-D6. The oscillating time is controlled by integrated circuits IC2 and IC3. The oscillator 42 consists of a NAND-gate n1, resistors R14-R22, and condensators IC1. The counter circuit 43 consists of an integrated circuit IC1. The control device circuit 44 consists of resistors R5-R13, transistors T3-T7, NAND-gates N2-N4 and the light diode 45 referred to as LDR1, and of the light sensitivity control 46, in the electric diagram referred to as P1, which as indicated is an adjustable resistor.

The voltage doubler 40 wherein the diodes D1-D6 and the condensators C3-C8 form an unstable multivibrator, doubles the voltage of the 1½ V voltage of the battery 1 to about 4.6 V which supplies the circuits. The control device 5 has a working voltage of 1½ V.

The oscillator circuit 42 oscillates around the resistor R14 parallel with R15. After the counter circuit 43 having counted 512 pulses from the oscillator circuit 42, leg no. 14 in the integrated circuit IC1 gets high, and the current supply to the control device is interrupted. Now a resting period 18 is started, and the oscillator circuit 42 oscillates only around the resistors R14. When this sequence has taken place either 512 or 1024 times dependent on the position of the change-over switches DIL 3 and DIL 4, leg no. 14 on the integrated circuit gets high and the resistor R16 is coupled parallel to the resistor R14 instead of the resistor R15. Thereafter a working period 17 is initiated, the length of which depends on the resistance value of the resistor R16.

After four different working periods 17, which are determined by the resistance values of the resistors R15, R16, R17 and R18, leg no. 1 in the integrated circuit IC2 gets high. The resistor R7 is coupled parallel to the resistor R5, whereby the control device 5 receives increased energy, so that in case the control device is a ventilator motor, said motor goes with a double speed, and in case of an electromagnet, said magnet gets an increased pulling force and consequently valve lifting height. The resistor R19 is coupled parallel to the resistor R14 which causes the resistor R19 to decide the resting period 18. When all resistors R15-R22 have been used, the process starts all over again.

The light sensitivity works that way that the darker the surroundings of the apparatus get, the greater resistor vaoue for the light diode 45 which in the diagram is marked LDR1. When said resistance is high enough, leg no. 4 in NAND-gate n2 gets high, and the current supply to the control device 5 is thus interrupted, as long as it is dark.

Furthermore, FIG. 12 shows that the integrated circuits IC1 and IC2 have international standard No. 4040, IC3 has No. 4051, IC4 has No. 4093, and NAND-gate n1–n4 has international standard No. 4093 for integrated circuits. On the top of the diagram are placed two electrolyte condensators C9 and C12. Leg no. 11 in the integrated circuit IC2 is connected to frame via a resistor R23.

We claim:

1. Method for dispensing an aromatic vapour to a space from a vapour dispensing substance by a dispensing device allowing the substance to be dispersed into a room comprising: providing an electronic control system, supplying electric current to the control system and from the control system to the dispensing device to cause the device to allow the vapour dispensing substance to be dispensed to the room, periodically cutting off the electric current from the control system to the dispensing device for pre-determined periods of time and gradually increasing the current supply to the dispensing device as the vapour dispensing substance is dissipated to maintain a constant level of vapour concentration until the vapour dispensing substance is used up.

2. The method of claim 1 wherein the current is increased by increasing the length of the current supply time to the dispensing device.

3. The method of claim 2 wherein the current intensity is also increased.

4. The method of claim 1 wherein the current is increased by decreasing the length of the periods of current cut-off.

5. The method of claim 4 wherein the current intensity is also increased.

6. The method of claim 1 wherein the current is increased by increasing the current intensity.

* * * * *